United States Patent [19]

Chamberlin

[11] Patent Number: 5,117,014
[45] Date of Patent: May 26, 1992

[54] PROCESS FOR THE PREPARATION OF 1-AMINO-4-BROMOANTHRAQUINONES

[75] Inventor: Kim S. Chamberlin, Kingsport, Tenn.

[73] Assignee: Eastman Kodak Company, Rochester, N.Y.

[21] Appl. No.: 694,612

[22] Filed: May 2, 1991

[51] Int. Cl.$^5$ .............................................. C07C 46/00
[52] U.S. Cl. ..................................... 552/249; 552/237
[58] Field of Search ................................ 552/249, 237

[56] References Cited

FOREIGN PATENT DOCUMENTS 0259909 12/1969 U.S.S.R. .............................. 552/249

OTHER PUBLICATIONS

*Organic Synthesis*, Coll. vol. 3, pp. 575–576, John Wiley & Son, Inc. (1955).
FIAT FINAI Report No. 1313, p. 222 (1948).

Primary Examiner—Marianne Cintins
Assistant Examiner—Jessica Nguyen
Attorney, Agent, or Firm—J. Frederick Thomsen; William P. Heath, Jr.

[57] ABSTRACT

Disclosed is a process for the preparation of 1-amino-4-bromoanthraquinones by the bromination of the corresponding 1-aminoanthraquinone wherein a 1-aminoanthraquinone is contacted with elemental bromine in the presence of a carboxylic acid solvent and added hydrobromic acid. The process is not as complicated as known processes and produces lower amounts of isomeric 1-amino-2-bromoanthraquinones.

5 Claims, No Drawings

PROCESS FOR THE PREPARATION OF 1-AMINO-4-BROMOANTHRAQUINONES

This invention pertains to a novel process for the preparation of 1-amino-4-bromoanthraquinones by the bromination of the corresponding 1-aminoanthraquinone. More specifically, this invention pertains to the preparation of 1-amino-4-bromoanthraquinones by contacting the corresponding 1-aminoanthraquinone with elemental bromine in the presence of a carboxylic acid solvent and added hydrobromic acid.

1-Amino-4-bromoanthraquinones was used extensively in the manufacture of colorant and dye compounds. For example, 1-methylamino-4-bromoanthraquinone may be reacted with various nucleophiles, e.g., amines, to produce red to blue disperse dyes used in the coloration of synthetic textile materials such as polyester fibers.

A procedure for the preparation of 1-methylamino-4-bromoanthraquinone by adding bromine to a solution of 1-methylaminoanthraquinone in pyridine is described Organic Synthesis, Coll. Vol 3, 575, John Wiley & Sons, Inc. (1955). The use of pyridine on a commercial scale is particularly undesirable because of its odor, cost and disposal problems it presents Another known procedure (FIAT Final Report No. 1313, 222, 1948) involves the steps of (1) dissolving 1-methylaminoanthraquinone in concentrated sulfuric acid, (2) drowning the resulting solution in a large quantity of water, (3) filtering, (4) adding the solids collected to a mixture of hydrochloric acid and water and, finally, adding a solution of bromine in hydrochloric acid.

The bromination of 1-aminoanthraquinones in a carboxylic acid using approximately an equimolar amount of elemental bromine typically gives a mixture of the desired 4-bromo isomer to 2-bromo isomer in a 4-isomer:2-isomer mole ratio of about 7:1. The formation of the 2-isomer not only represents a loss in yield from the 1-aminoanthraquinone reactant but also can require purification of the bromination product depending, for example, on the use for which the 1-amino 4-bromoanthraquinone is intended.

I have discovered an improved process for the bromination of 1-aminoanthraquinones whereby the mole ratio of 4-isomer:2-isomer is increased substantially, e.g., 4-isomer:2-isomer mole ratios of at least 15:1 and typically as high as 18:1 to 20:1, depending upon the particular anthraquinone reactant employed. The process of the present invention provides a means for the preparation of anthraquinone compounds having the formula

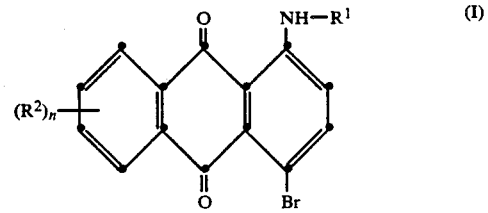

(I)

by adding elemental bromine (Br$_2$) to a mixture of an anthraquinone reactant having the formula

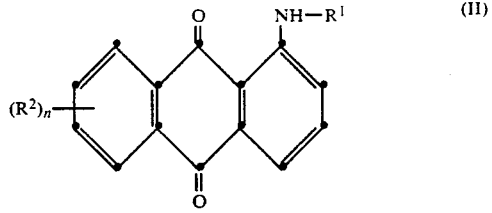

(II)

hydrogen bromide, and a lower carboxylic acid at a temperature of 25° C. or less, wherein:

the mole ratio of hydrobromic acid:anthraquinone reactant is at least 0.5:1 at the commencement of the bromine addition;

R$^1$ is hydrogen or an alkyl or cycloalkyl radical;

R$^2$ is an alkyl radical, a cycloalkyl radical, halogen or —NH—R$^1$; and n is 0, 1 or 2.

The bromination process provided by my invention occurs in a heterogeneous system wherein a substantial amount of the anthraquinone reactant exists as a slurry or dispersion in the carboxylic acid. The lower carboxylic acid employed as the reaction medium may be selected from aliphatic carboxylic acids having about 2 to 4 carbon atoms, especially acetic acid, propionic acid or a mixture thereof. Since the freezing point of acetic acid is 16.6° C., when the process is carried out within the preferred temperature range, acetic acid must be used in combination with one or more other carboxylic acids. The preferred reaction medium or diluent comprises a mixture of acetic and propionic acids, e.g., in acetic:propionic weight ratios of about 4:1 to 1:1. The amount of carboxylic acid used is not critical and can be varied substantially e.g., amounts which give carboxylic acid:anthraquinone reactant weight ratios in the range of about 9:1 to 25:1. The carboxylic acid:-anthraquinone reactant weight ratio normally is in the range of about 10:1 to 12:1.

The hydrogen bromide may be provided to the process in the form of an aqueous solution, e.g., hydrobromic acid having a HBr concentration of about 30 to 65, preferably about 40 to 50 weight percent. The amount of hydrogen bromide present in the reaction mixture when the bromine addition is commenced normally should be at least 0.5 mole per mole of anthraquinone reactant. The use of hydrogen bromide concentrations in substantial stoichiometric excess relative to the reactant is not detrimental to the bromination process but produces no benefit. The amount of hydrogen bromide initially present preferably gives a hydrogen bromide:anthraquinone mole ratio of about 0.5:1 to 1.5:1.

The amount of elemental bromine added over the course of the reaction in accordance with my novel process normally is about 1.0 to 1.2 mole Br$_2$ per mole of anthraquinone reactant. The use of lesser amounts of bromine results in an unsatisfactory degree of reactant conversion whereas larger amounts causes the formation of excessive amounts of dibrominated by product, i.e., 1-amino-2,4-dibromoanthraquinones. The elemental bromine may be added as essentially pure bromine or as a mixture with an inert diluent such as one or more of the carboxylic acids described above. Typically, the bromine is added to a vigorously agitated, cooled mixture of the anthraquinone reactant, the hydrogen bromide and the carboxylic acid (or mixture of carboxylic acids) at a controlled rate to prevent the heat of reaction from increasing the process temperature above the desired temperature range. The bromine addition usually is completed within about 45 to 60 minutes although the rate of addition may be faster or slower depending upon the particular operating procedure and equipment used and the efficiency of the heat dissipation provided thereby.

The bromination process is performed at temperatures of less than about 25° C. to suppress formation of undue amounts of undesired by-products. Generally, the selectivity to the desired 4-bromo product increases with lower temperatures. Also, the amount of bromine lost to the atmosphere during the practice of the process decreases with lower temperatures. Thus, the process preferably is carried out at a temperature of less than about 5° C. with a temperature range of about 0 to 5° C. being particularly preferred.

The alkyl and cycloalkyl groups represented by $R^1$ and $R^2$ in formulas (I) and (II) may be unsubstituted or substituted alkyl of up to about 12 carbon atoms or unsubstituted or substituted cycloalkyl containing 5 to 7 ring carbon atoms. Examples of the substituents which may be present on the substituted alkyl groups include alkoxy of up to about 4 carbon atoms, e.g., methoxy, ethoxy and butoxy; alkanoyloxy of up to about 4 carbon atoms, e.g., acetoxy; hydroxy; cyano; alkanoylamino, e.g., acetylamino (acetamido); and the like. The —NH—$R^1$ groups which $R^2$ may represent may be the same as or different from the —NH—$R^1$ at the 1-position of the anthraquinone nucleus.

The advantages provided by the present invention, e.g., the improved 4-isomer:2-isomer ratios, are most significant when the anthraquinone reactant has the structure:

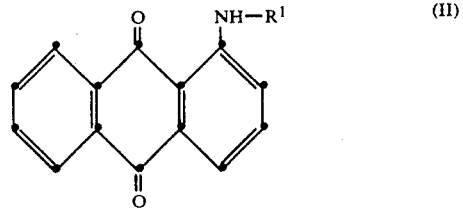

wherein $R^1$ is an alkyl or cycloalkyl radical, preferably unsubstituted alkyl of up to about 6 carbon atoms such as methyl ethyl, propyl, isopropyl, butyl, isobutyl, hexyl and the like.

My novel process is further illustrated by the following example wherein parts are by weight unless specified otherwise. The 1-methylaminoanthraquinone reactant used in the examples contained approximately 0.95 weight percent 1-aminoanthraquinone.

EXAMPLE 1

A vigorously agitated mixture of acetic acid (135.8 parts), propionic acid (74.5 parts), 48% hydrobromic acid (12.8 parts, 0.076 mole) and 1-methyl-aminoanthraquinone (18.0 parts, 0.076 mole) is cooled to 0 to 5° C. Bromine (13.3 parts, 0.083 mole) is added to the mixture over a period of about 1 hour at a rate of 2.2 to 2.5 parts per 10 minutes while maintaining the temperature of the mixture at 0 to 5° C. Agitation of the mixture is continued for 1 hour after addition of the bromine is completed and then ice (180 parts), water (173 parts) and a solution of sodium metabisulfite (5 parts) in water (24 parts) is added to the reaction mixture at 0 to 5° C.

The mixture then is agitated for approximately 45 minutes and the product is isolated by filtration and dried.

This procedure was repeated 5 times substantially as described. The average yield of product obtained was 22.9 parts (95.4% of theory). The average composition of the product, determined by liquid chromatography, was:

| | |
|---|---|
| 1-methylamino-4-bromoanthraquinone | 95.6% |
| 1-methylamino-2-bromoanthraquinone | 0.2% |
| 1-methylamino-2,4-dibromoanthraquinone | 0.4% |
| 1-methylaminoanthraquinone | 2.8% |

Due to its solubility in the final reaction medium, most of the 1-methylamino-2-bromoanthraquinone is not recovered in the product. The product also contained about 0.3% total of 1-amino-4-bromoanthraquinone and 1-amino-2,4-dibromoanthraquinone.

EXAMPLE 2

A vigorously agitated mixture of acetic acid (85 mL), propionic acid (50 mL), 48% hydrobromic acid (8.5 parts, 0.0504 mole) and 1-methylaminoanthraquinone (12.35 parts, 0.05 mole) is cooled to 0 to 5° C. A mixture (20 mL) of acetic acid and bromine (8.75 parts, 0.0547 mole) is added to the mixture over a period of about 1 hour while maintaining the temperature of the mixture at 0 to 5° C. Samples of the reaction mixture were taken (1) after 2 mL of the bromine containing mixture had been added, (2) after 10 mL of the bromine-containing mixture had been added, (3) after 15 mL of the bromine mixture had been added and (4) 5 minutes after 20 mL of the bromine containing mixture had been added. The samples were analyzed by liquid chromatography. The results of the analyses, reported in area percent, are shown below wherein AQ means anthraquinone.

| | Sample | | | |
|---|---|---|---|---|
| Component | (1) | (2) | (3) | (4) |
| 1-Methylamino-4-bromo-AQ | 44.10 | 57.35 | 83.59 | 94.12 |
| 1-Methylamino-2-bromo-AQ | 2.56 | 3.05 | 4.06 | 0.72 |
| 1-Methylamino-2,4-dibromo-AQ | 0 | 0 | 0.50 | 3.16 |
| 1-Methylamino-AQ | 51.22 | 37.82 | 9.72 | 0.76 |

The 1-methylaminoanthraquinone reactant contained some 1-aminoanthraquinone resulting in the presence of minor amounts of 1-amino-4-bromoanthraquinone and 1-amino-2,4-dibromoanthraquinone in the final reaction mixture.

COMPARATIVE EXAMPLE 1

The bromination procedure, sampling and analyses described in Example 2 were repeated except that no hydrogen bromide was added to the mixture to which the bromine was added. The results of the analyses, reported in the area percent, as shown below wherein AQ means anthraquinone.

| | Sample | | | |
|---|---|---|---|---|
| Component | (1) | (2) | (3) | (4) |
| 1-Methylamino-4-bromo-AQ | 3.58 | 52.47 | 71.39 | 83.33 |
| 1-Methylamino-2-bromo-AQ | 1.00 | 5.01 | 5.50 | 6.41 |
| 1-Methylamino-2,4-dibromo-AQ | 0 | 0 | 0.13 | 0.38 |
| 1-Methylamino-AQ | 93.51 | 40.14 | 20.46 | 7.32 |

The 1-methylaminoanthraquinone reactant contained some 1-aminoanthraquinone resulting in the presence of minor amounts of 1-amino-4-bromoanthraquinone and 1-amino-2,4-dibromoanthraquinone in the final reaction mixture.

COMPARATIVE EXAMPLE 2

The bromination procedure, sampling and analyses described in Example 2 were repeated except that 32% hydrochloric acid (4.0 g, 0.035 mole HCl) was added to the mixture to which the bromine was added. The results of the analyses, reported in area percent, are shown below wherein AQ means anthraquinone.

| Component | Sample | | | |
|---|---|---|---|---|
| | (1) | (2) | (3) | (4) |
| 1-Methylamino-4-bromo-AQ | 9.14 | — | 66.87 | 78.68 |
| 1-Methylamino-2-bromo-AQ | 1.81 | — | 8.19 | 10.60 |
| 1-Methylamino-2,4-dibromo-AQ | 0 | — | 0.31 | 0.48 |
| 1-Methylamino-AQ | 87.17 | — | 23.06 | 8.61 |

The 1-methylaminoanthraquinone reactant contained some 1-aminoanthraquinone resulting in the presence of minor amounts of 1-amino-4-bromoanthraquinone and 1-amino-2,4-dibromoanthraquinone in the final reaction mixture.

EXAMPLE 3

A vigorously agitated mixture of acetic acid (85 mL), propionic acid (50 mL), 48% hydrobromic acid (8.75 parts, 0.0547 mole) and 1-aminoanthraquinone (11.16 parts, 0.05 mole) is cooled to 0 to 5° C. The 1-aminoanthraquinone used contained 8-9% of 1,X-diaminoanthraquinone impurity. A mixture (20 mL) of acetic acid and bromine (8.75 parts, 0.0547 mole) is added to the mixture over a period of about 1 hour while maintaining the temperature of the mixture at 0 to 5° C. Samples of the reaction mixture were taken (1) after 2 mL of the bromine containing mixture had been added, (2) after 10 mL of the bromine containing mixture had been added and (3) 5 minutes after 20 mL of the bromine-containing mixture had been added. Water (120 mL) was added to the mixture to precipitate the product which was collected by filtration, washed first with water and then with isopropanol and dried. The crude product weighed 12.92 g. The three samples of the reaction mixture and the crude product were analyzed by liquid chromatography. The results of the analyses, reported in area percent, are shown below wherein AQ means anthraquinone.

| Component | Sample | | | |
|---|---|---|---|---|
| | (1) | (2) | (3) | Product |
| 1-Amino-4-bromo-AQ | 2.81 | 19.04 | 45.13 | 76.23 |
| 1-Amino-2-bromo-AQ | 1.72 | 2.83 | 6.19 | 2.82 |
| 1-Amino-2,4-dibromo-AQ | 0.73 | 8.61 | 17.04 | 11.27 |
| 1,X-Diamino-4-bromo-AQ | 0.92 | 4.15 | 5.79 | 4.12 |
| 1-Amino-AQ | 87.75 | 62.05 | 25.45 | 3.75 |
| 1,X-Diamino-AQ | 6.07 | 2.19 | 0 | 0 |

The invention has been described in detail with particular reference to preferred embodiments thereof, but it will be understood that variations and modifications may be effected within the spirit and scope of the invention.

I claim:

1. Process for the preparation of anthraquinone compounds having the formula

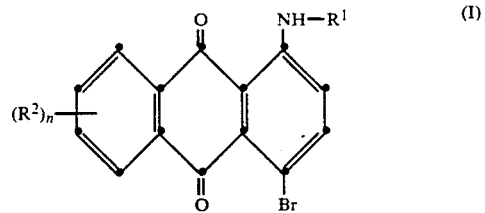

which comprises adding elemental bromine to a mixture of an anthraquinone reactant having the formula

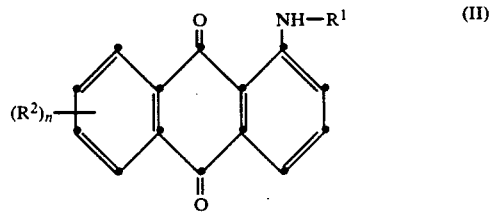

hydrogen bromine, and one or more lower carboxylic acids at a temperature of 25° C. or less, wherein:

the mole ratio of hydrogen bromide:anthraquinone reactant is at least 0.5:1 at the commencement of the bromine addition;

$R^1$ is hydrogen or an alkyl or cycloalkyl radical;

$R^2$ is an alkyl radical, a cycloalkyl radical, halogen or —NH—$R^1$; and n is 0, 1 or 2.

2. Process according to claim 1 wherein the mole ratio of hydrogen bromide anthraquinone reactant is about 0.5:1 to 1.5:1 at the commencement of the bromine addition, the amount of elemental bromine added is about 1.0 to 1.2 mole $Br_2$ per mole of anthraquinone reactant and the process is carried out at a temperature of about 5 to 25° C.

3. Process according to claim 2 wherein the lower carboxylic acid is a mixture of acetic acid and propionic acid in which the acetic:propionic weight ratio is about 4:1 to 1:1.

4. Process for the preparation of an anthraquinone compounds having the formula which comprises adding elemental bromine to a mixture of an anthraquinone reactant having the formula

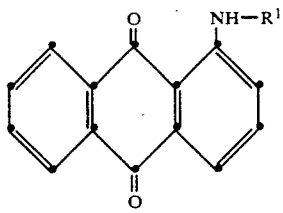

hydrogen bromide, and one or more lower carboxylic acids at a temperature of about 5 to 25° C., wherein:
the mole ratio of hydrogen bromide reactant is about 0.5:1 ti 1.5 at the commencement of the bromine addition; and
$R^1$ is hydrogen or an alkyl or cycloalkyl radical.

5. Process according to claim 4 wherein the amount of elemental bromine added is about 1.0 to 1.2 mole Br, per mole of anthraquinone reactant and the lower carboxylic acid is a mixture of acetic acid and propionic acid in which the acetic:propionic weight ratio is about 4:1 to 1:1.

* * * * *